United States Patent [19]
Mjalli

[11] Patent Number: 6,117,940
[45] Date of Patent: Sep. 12, 2000

[54] AMINO-KETONE SOLID SUPPORT TEMPLATES

[76] Inventor: Adnan M. M. Mjalli, 7393 Wolfspring Trace, Louisville, Ky. 40241

[21] Appl. No.: 09/174,521

[22] Filed: Oct. 16, 1998

Related U.S. Application Data

[60] Provisional application No. 60/061,927, Oct. 17, 1997.

[51] Int. Cl.[7] .................. C08F 283/00; C08G 63/48; C08K 5/07; G01N 33/00
[52] U.S. Cl. .................. 525/54.11; 525/54.21; 525/55; 525/153; 525/157; 525/257; 525/259; 436/111; 436/128
[58] Field of Search ............... 525/54.11, 54.21, 525/55, 153, 157, 257, 259; 436/111, 128

[56] References Cited

U.S. PATENT DOCUMENTS 4,267,344  5/1981  Halstrom et al. .................. 548/227

*Primary Examiner*—Nathan M. Nutter

[57] ABSTRACT

A solid support template for solid phase synthesis of amino group containing compounds is provided that comprises amino-ketone core compounds of the general formula:

$$A\text{-}L\text{-}NH(CR_1R_2)_n COR_3$$

linked to appropriate insoluble substrates to create solid support templates having the general formula:

$$\text{Polymer-}X\text{-}L\text{-}NH(CR_1R_2)_n COR_3$$

where L is a multifunctional monomer carrying a first functional group that forms a covalent bond with X and a second functional group comprising an amine and L, $R_1$, $R_2$ and $R_3$ are selected from the group consisting of alkyl, alkyl-aryl, alkenyl, alkenyl-aryl groups having up to 6 carbon atoms and substituted forms thereof. The amino-ketone templates are useful for the solid phase synthesis of compounds such as the imidazoles, benzodiazepines, pyrazines, and steroid mimics.

29 Claims, No Drawings

AMINO-KETONE SOLID SUPPORT TEMPLATES

CROSS REFERENCE TO RELATED APPLICATION

This application claims the benefit of Provisional Application 60/061,927, filed Oct. 17, 1997 in the name of Adnan M. M. Mjalli.

FIELD OF THE INVENTION

The present invention relates to amino-ketone templates linked to insoluble materials and methods for producing products generated through a plurality of chemical reactions utilizing amino-ketone templates on solid support.

BACKGROUND OF THE INVENTION

The use of solid phase synthesis techniques for the synthesis of polypeptides and oligonucleotides is well known in the art. More recently, the use of solid phase techniques for the synthesis of small organic molecules has become a major focus of research. Of prime importance has been the ability of solid phase techniques to be automated, with an attendant increase in compound throughput and efficiency in research. This has been exploited with great vigor in the area of pharmaceutical research where it has been estimated that 10,000 compounds must be synthesized and tested in order to find one new drug (Science, 259, 1564, 1993). The focus on combinatorial chemistry techniques to increase compound throughput has now become almost universal in the pharmaceutical and agricultural industries.

An additional aspect relates to the chemical diversity of the compound stocks that are available for screening in pharmaceutical companies in the search for new lead structures. These have tended to be limited to the classes of compounds previously investigated through medicinal chemical techniques within each company. Therefore the availability of new classes of molecules for screening has become a major need.

The movement of a chemical reaction from a single reaction in a flask to an experiment producing hundreds or thousands of molecules of varied structure simultaneously in a robot in not a simple process. Consequently, although many classes of organic reactions have now been shown to work on solid phase, a great deal of research is required in order to optimize each new reaction that a chemist wants to undergo this conversion. This optimization phase has become the major stumbling block and the major time-consuming element in modern solid phase combinatorial chemistry research.

In view of the above, the field of pharmaceutical and agricultural research has a strong need for highly flexible routes to novel classes of compounds for screening and clinical testing. The principle object of this patent is to provide an exceptionally flexible process for the high throughput production of many classes of organic molecules. Some of the chemical ring systems attainable through this technology are completely novel and some of the ring systems have value as known, pharmacologically useful agents.

SUMMARY OF THE INVENTION

The present invention relates to amino-ketone core compounds of the general formula:

A-L-NH(CR$_1$R2)$_n$COR$_3$ linked to appropriate insoluble substrates to create solid support templates of Formula 1.

Polymer-X-L—NH(CR$_1$R$_2$)$_n$COR$_3$     (Formula 1)

Amino-ketone core compounds allow for the production of compounds that heretofore have not been prepared or prepared with great difficulty and expense. However, subjecting such amino-ketone core compounds to a series of chemical reactions in order to create useful compounds using conventional solution chemistry is not practical due to their chemical reactivity. In solution, amino ketone molecules have the ability to undergo self condensation reactions (one molecule would react with another molecule through the amine or the carbonyl moieties) which lead to various complications in the desired chemical transformations. For example, as illustrated by Scheme 1 below, attempts to react 1-methylamino-butan-2-one A with N-methyl benzyl amine in the presence of an acid provided a mixture of reaction products. Compound B resulted from a self-condensation reaction between two molecules of compound A

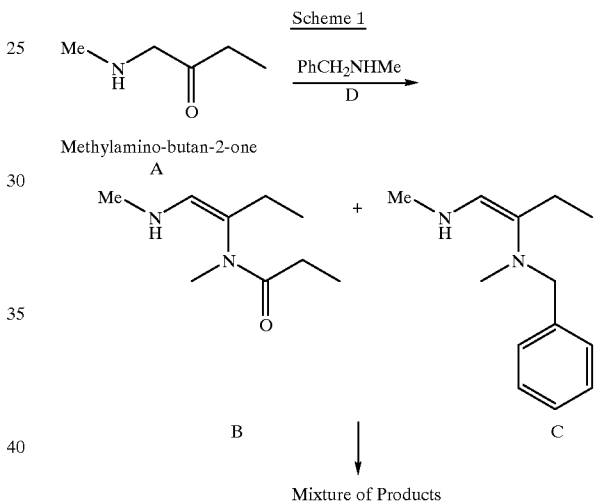

These types of self-condensation reactions can be initiated under neutral, acidic or basic conditions. Although highly suited for use in the production of a variety of therapeutic products, the use of amino-ketones in solution chemistry to create useful compounds has been very limited because of the formation of mixed products as discussed above.

The present invention provides a solution to this problem by having the amino ketone linked to a suitable polymer to create intermediate compounds of Formula 1 that are then further reacted in accordance with solid support methods to form the desired compound. By linkage of the self-reactive amino ketone molecule to a polymer, one achieves isolation of that molecule from other like molecules and one is thereby able to carry out only the desired modifications on said intermediate with other reagents. Thus, a person who is skilled in the art of organic chemistry then is able to assemble therapeutically useful compounds through a plurality of chemical transformations using templates of Formula 1. This strategy will circumvent the inherent problems and limitations associated with the attempted use of amino ketone chemistry in solution.

In accordance with the invention amino-ketone compounds of general Formula 1 are synthesized according to the following general reaction Scheme 2

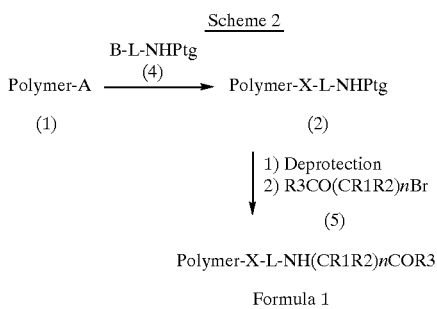

Formula 1 sequence:

Reaction of polymer-A (1) with a series of monomers (4) in which the NH group is protected. The reaction is carried out in the presence of the appropriate reagents to form compound (2) which undergo alkylation with $R_3CO(CR_1R_2)_nBr$, (5) (n=1, 2), to provide the desired solid support polymeric template of Formula 1.

This invention further relates to a method utilizing the novel amino-ketone templates of the invention for the production of compounds for screening as therapeutically useful compounds.

The ease of purification and automation of solid support synthesis of peptides (Atherton, E.; Sheppard, RC; Solid Phase Peptide Synthesis: A Practical Approach; IRL Press at Oxford University Press: Oxford 1989) and non-peptide-based molecules (Lenzoff, C.C.; *Acc. Chem. Res.*, 1978, 11, 327–333) gives several advantages to solid support synthesis over solution chemistry. Solid support synthesis of combinatorial libraries has yielded many biologically active compounds (Moos, W. H. et al.; *Annu. Rep. Med. Chem.*, 1993, 28, 315–324; Terrett, N. K.; Gardner, M.; Gordon, D. W.; Kobylecki, R. J.; Steele, J.; Tetrahedron 1995, 51, 8135–73).

Solid support synthesis is carried out on a substrate consisting of a polymer, cross-linked polymer, functionalized polymeric pin, or other insoluble material. These polymers or insoluble materials have been described in literature and are known to those who are skilled in the art of solid phase synthesis (Stewart J M, Young J. D.; Solid Phase Peptide Synthesis, 2nd Ed; Pierce Chemical Company: Rockford. Ill., 1984). Some of them are based on polymeric organic substrates such as polyethylene, polystyrene, polypropylene, polyethylene glycol, polyacrylamide, and cellulose. Additional types of supports include composite structures such as grafted copolymers and polymeric substrates such as polyacrylamide supported within an inorganic matrix such as kieselghuhr particles, silica gel, and controlled pore glass.

Such polymers are substituted with linkers that modulate the stability of the linkage to the resin. The linkers incorporate reactive functionalities (A), (e.g. amino, hydroxy, oximino, phenolic, silyl, etc.) for loading of monomers suitable for carrying out a plurality of further reactions to synthesize the desired products (Hemkens, P. H. H.; Ottenheijm, H. C. J.; Rees, D.; Tetrahedron Lett. 1996, 52, 4527–54).

Examples of suitable support resins and linkers are given in various reviews (Barany, G.; Merrifield, R. B. "Solid Phase Peptide Synthesis", in "The Peptides—Analysis, Synthesis, Biology. Vol 2," [Gross, E. and Meienhofer, J., Eds.], Academic Press, Inc., New York, 1979, pp 1–284; Backes, B. J.; Ellman, J. A. Curr. Opin. Chem. Biol. 1997. 1, 86.) and in commercial catalogs (Advanced ChemTech, Louisville, Ky.; Novabiochem, San Diego, Calif.). Some examples of particularly useful functionalized resin/linker combinations that are meant to be illustrative and not limiting in scope are shown below:

1 Merrifield resin—Chloromethyl co-poly(styrene-1 or 2%-divinylbenzene) which can be represented as:

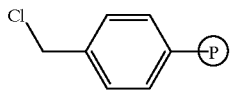

2 Benzhydrylamine copoly(styrene-1 or 2%-divinylbenzene) which referred to as the BHA resin

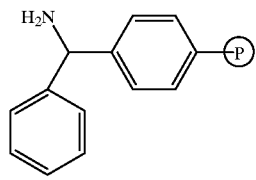

3 Methyl benzhydrylamine copoly(styrene-1 or 2%-divinylbenzene) which to as MBHA and represented as:

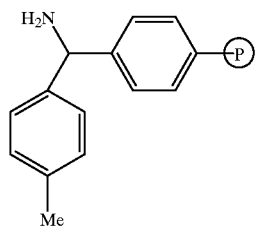

4. Argogel resins

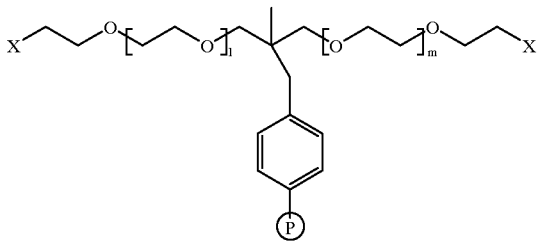

Some additional resins that are useful in specialized situations are:

5. Trityl and functionalized Trityl resins, such as 2-chlorotrityl resin (Barlos, K.; Gatos, D.; Papapholiu, G.; Schafer, W.; Wenqing, Y.; Tetrahedron Lett. 989, 30, 3947).

6. Sieber amide resin (Sieber, P.; Tetrahedron Lett. 1987, 28, 2107).

7. Wang resin (Wang, S. S.; J. Am. Chem. Soc. 1973, 95, 1328–1333).

8. Oxime resin (DeGrado, W. F.; Kaiser, E. T.; J. Org. Chem. 1982, 47, 3258).

9. Polyoxyethylene grafted (Tentagel) resins (Rapp, W.; Zhang, L.; Habich, R.; Bayer, E. in "Peptides 1988; Proc. 20$^{tth}$ European Peptide Symposium" [Jung, G. and Bayer, E., Eds.], Walter de Gruyter, Berlin, 1989, pp 99–201).

10. Safety catch resins (see resin reviews above; Backes, B. J.; Virgilio, A. A.; Ellman, J. A.; J. Am. Chem. Soc. 1996, 118, 3055–6).

11. Photolabile resins (e.g. Abraham, N. A. et al.; Tetrahedron Lett. 1991, 32, 577).
12. Rink acid resin (Rink, H.; Tetrahedron Lett. 1987, 28, 3787).
13. HPPB-BHA resin (4-hydroxymethyl-3-methoxyphenoxybutyric acid-BHA Florsheimer, A.; Riniker, B. in "Peptides 1990; Proceedings of the 21$^{st}$ European Peptide Symposium" [Giralt, E. and Andreu, D. Eds.], ESCOM, Leiden, 1991, pp 131).
14. Resins with silicon linkage (Chenera, B.; Finkelstein, J. A., Veber, D. F.; J. Am. Chem. Soc. 1995, 117, 11999–12000; Woolard, F. X.; Paetsch, J.; Ellman, J. A.; J. Org. Chem. 1997, 62, 6102–3).
15. PEGA resins (Bis 2-acrylamidoprop-1-yl polyethyleneglycol crosslinked dimethyl acrylamide and acryloyl sarcosine methyl ester) (Meldal, M.; Tetrahedron Letters 1992, 33, 3077).

Another type of solid phase synthesis method is the "pin method" developed by Geysen et al., for combinatorial solid-phase peptide synthesis (Geysen et al.; J. Immunol. Meth. (1987) 102:259–274). According to this method, as it may be practiced in the present invention, a series of 96 pins are mounted on a block in an arrangement and spacing which correspond to a 96-well microtiter reaction plate, and the surface of each pin is derivatized to contain a terminal linker functional groups. The pin block is then lowered into a series of reaction plates to immerse the pins in the wells of the plates where coupling occurs at the terminal linker functional groups, and a plurality of further reactions are carried out in a similar fashion.

Reagents varying in their substituent groups occupy the wells of each plate in a predetermined array, to achieve as ultimate products, a unique product on each pin. By using different combinations of substituents, one achieves a large number of different compounds with an array of central core structures.

A related method of synthesis uses porous polyethylene bags (Tea Bag method) containing the functionalized solid phase resins referred to above (Houghton, R. A., et al., Nature, 354, 84–86, 1991). These bags of resin can be moved from one reaction vessel to another in order to undergo a series of reaction steps for the synthesis of libraries of products.

For purposes of this patent, we also define the use of solubilizable resins that can be rendered insoluble during the synthesis process as Solid Phase supports. Although this technique is frequently referred to as "Liquid Phase Synthesis", the critical aspect for our process is the isolation of individual amino ketone molecules from each other on the resin and the ability to wash away excess reagents following a reaction sequence. This also is achieved by attachment to resins that can be solubilized under certain solvent and reaction conditions and rendered insoluble for isolation of reaction products from reagents. This latter approach, (Vandersteen, A. M.; Han, H.; Janda, K. D.; Molecular Diversity, 1996, 2, 89–96.) uses high molecular weight polyethyleneglycol as a solubilizable polymeric support and its use is also incorporated into this patent.

Among the reaction sequences carried out by the method of the present invention is the formation of the amide bond. Many suitable reagents are known to the art to be suitable for this reaction sequence (i.e. Stewart J M, Young J. D.; Solid Phase Peptide Synthesis, 2nd Ed; Pierce Chemical Company: Rockford. Ill., 1984). Among the many reagents available, some particularly useful reagents are: dialkylcarbodiimide with an additive such as 1-hydroxybenzotriazole, especially diisopropylcarbodiimide/1-hydroxy-7-azabenzotriazole and the like (DIC/HABT); benzotriazol-1-yloxytris-(dimethylamino)-phosphonium hexafluorophosphate (BOP); O-benzotriazolo-N,N,N',N'-tetramethyluronium hexafluorophosphate (HBTU); Bromo-tris-pyrrolidinophosphonium hexafluorophosphate (PyBrOP), Fmoc amino acid fluorides (Carpino, L. A., et al. 9-Fluoroenylmethyloxycarbonyl (FMOC) Amino Acid Fluorides. Convenient New Peptide Coupling Reagents Applicable to the FMOC/tert-Butyl Strategy For Solution and Solid-Phase Synthesis, J. Am. Chem.Soc., 1990, 112, pp 9651–2) and the like. The degree of steric hindrance, reactivity of the amine, and other factors may determine which reagent will be most suitable for a particular substrate, but many of the reagents will give a suitable result for most reactions.

As is conventional, the amide group is protected until it is to be utilized in a reaction sequence. Those skilled in the art will appreciate that any of the wide variety of available amino protecting groups may be used such as the tert-Butyloxycarbonyl (Boc), Fluorenylmethyloxycarbonyl (Fmoc), and the like. The choice of a particular protecting group will depend on the specific nature of the substituents and reactions contemplated. Also, more than one type of protecting group may be necessary at any given point in the synthesis (see, e.g., Green, T. and Wuts, P. G. M.; Protective Groups In Organic Synthesis 2$^{ND}$ ED., Wiley, 1991 and references therein).

Cleavage from the solid support can be carried out using one of a number of well-known and convenient procedures (e.g. Stewart, J. M.; Young J. D.; Solid Phase Peptide Synthesis, 2nd Ed; Pierce Chemical Company: Rockford. Ill., 1984; Barany, G.; Merrifield, R. B. "Solid Phase Peptide Synthesis", in "The Peptides—Analysis, Synthesis, Biology. Vol 2," [Gross, E. and Meienhofer, J., Eds.], Academic Press, Inc., New York, 1979, pp 1–284). Among these procedures are various acidolytic, based-catalyzed, reductive, photolytic, and self-cleavage techniques.

The conditions used for the popular acidolytic cleavage procedures depends on the particular choice of resin/linker combination used for the synthesis. For example, cleavage may be carried out under conditions utilizing HOAc/CH$_2$Cl$_2$ (Rink Acid resin), 5% CF$_3$CO$_2$H (2-chlorotrityl resin), 25% CF$_3$CO$_2$H (Wang resin), anhydrous HF or mixtures of CF$_3$SO$_3$H/CF$_3$CO$_2$H (Merrifield resin). Ester resin linkages can be cleaved under nucleophilic conditions to yield, for example, amides (R-NH2/CH$_3$OH), esters (CH$_3$OH/Et$_3$N), hydrazides (N$_2$H$_4$/DMF), etc. Catalytic transfer hydrogenation (Pd[OAc]$_2$/HCO$_2$H) has been used to reductively cleave esters from benzylic linkages on resins (Babiker, E.; Anantharamaiah, G. M.; Royer, G. P.; Means; G. E. J. Org. Chem. 1979, 44, 3442–4). A particularly useful nucleophilic cleavage entails a self-cleavage by a functional group in the molecule being synthesized, leading to the formation of a ring system. An example would be attack by an amine function in the compound being synthesized upon the ester linkage to the resin to lead to a new amide function in the target molecule. Such a cleavage step has advantages in that no harsh reagents are required and it may serve as a purification step since impurities lacking the amino function will not be cleaved from the resin. The above examples are merely illustrative of the many suitable cleavage techniques that are documented in review articles such as those above, are well known to those skilled in the art of solid phase synthesis, and are meant to illustrate but not limit the scope of the disclosure.

DESCRIPTION OF THE PREFERRED EMBODIMENTS

The solid phase component of the present invention comprises base substrates of the general Formula 1:

(Formula 1)

Wherein:
1) Polymer comprises insoluble materials (in aqueous or organic solvents) including those known in the art have been described in literature and are known to those who are skilled in the art of solid phase synthesis (Stewart, J. M.; Young J. D.; Solid phase Peptide Synthesis, 2nd Ed; Pierce Chemical Company: Rockford. Ill., 1984). Some of them are inorganic substrates such as Kieselghur, Silica gel, controlled pore glass and some are polymeric organic substrates such as polystyrene, polypropylene, polyethylene glycol, polyacrylamide, and cellulose. They may also exist as a composite of inorganic/polymeric substrates such as polyacrylamide supported within a matrix of kieselghuhr particles. The polymer has reactive functional groups which are used as handles for linkage to the monomer, such as amino, hydroxy, oximo, phenolic functionalities, etc.

(2) X is the atom or functional group connecting the polymer described in 1 and the template -L-NH $(CR_1R_2)_n COR_3$ and has a structure such as but not limited to:
   (a) Oxygen
   (b) Ester
   (c) Amide
   (d) Sulfur
   (e) Silicon
   (f) Carbon (3) L is a suitable multifunctional chemical monomer in which one functional group reacts with the polymer to form a covalent bond (X) and the other functional groups react with the appropriate reagents through a plurality of chemical reactions to provide the desired templates for further chemistry ($NH_2$). Both X and $NH_2$ can be represented within a suitable monomer L, such as in an amino acid. An example of a monomer that contains the X-L-$NH_2$ structure is Fmoc phenylalanine (Fmoc-Phe). Fmoc-Phe has two reactive functional groups the COOH and the Fmoc protected amine. Fmoc-Phe reacts with Merrifield resin under standard conditions to provide template 1c

Polymer-OCO—CH(CH2Ph)NH(CR$_1$R$_2$)COR$_3$ (Template 1c)

wherein from formula 1 X is OCO, and L is CH(CH$_2$Ph)NH

L also can be a non-amino acid such as for example, but not limited to, 4-hydroxyaniline (4-HO—C$_6$H$_4$—NH$_2$) which reacts with Merrifield resin using the Mitsunobu reaction and undergoes further reaction with an alkylating agent to provide compounds of template 1d

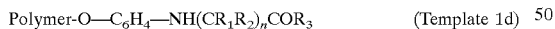

Polymer-O—C$_6$H$_4$—NH(CR$_1$R$_2$)$_n$COR$_3$ (Template 1d)

wherein O represents X and 4-C$_6$H$_4$NH represents L in Formula 1.

4) n=1 and 2
5) $R_1$ and $R_2$ and $R_5$ are independently selected from:
   (a) H
   (b) C1–C6 substituted alkyl, C1–C6-substituted alkyl-aryl C1–C6 substituted alkenyl, C1–C6 substituted alkenyl aryl wherein the substituents are selected from:
      i. H
      ii. chloro, fluoro, bromo, iodo, nitro, cyano, amino
      iii. C1–C6 alkyloxy
      iv. C1–C6 alkyloxy aryl,
      v. C1–C6 aminoalkyl, C1–C6 alkylamino
      vi. C1–C6 aminoalkyl aryl
      vii. C1–C6 aminocarbonyl
      viii. C1–C6 aminocarbonylalkyl-aryl
      ix. C1–C6 thioalkyl
      x. C1–C6 thioalkyl-aryl
      xi. C1–C6 alkylsulfoxide, C1–C6 alkylsulfone
      xii. C1–C6 alkylsulfonamide
      xiii. C1–C6 alkylsulfonamide aryl
      xiv. C1–C6 alkylsulfoxide aryl, C1–C6 alkylsulfone aryl
      xv. C1–C6 alkyl aminocarbonylamino C1–C6 alkyl, C1–C6 alkyl aminocarbonylamino C1–C6 alkyl aryl
      xvi. C1–C6 alkyloxycarbonyl C1–C6 alkyl, C1–C6 alkyloxy-carbonyl C1–C6 alkyl aryl
      xvii. C1–C6 carboxyalkyl, C1–C6 carboxyalkyl aryl
      xviii. C1–C6 carbonylalkyl, C1–C6 carbonylalkyl aryl
      xix. C1–C6 alkyloxycarbonylamino alkyl, C1–C6 alkyl-oxycarbonylamino alkyl aryl
      xx. Guanidino
      xxi. C1–C6 alkylCOOH, C1–C6 alkylCONH$_2$
      xxii. C1–C6 alkenylCOOH, C1–C6 alkenyl CONH$_2$
      and the like.
   (c) The aryl group described above is mono, di- and tri-substituted when the substituents are selected from 5b and the aryl group is selected from:
      (i) Phenyl
      (ii) Biphenyl
      (iii) 2-napthyl
      (iv) 1-napthyl
      (v) pyridyl
      (vi) furyl
      (vii) thiophenyl
      (viii) indolyl
      (ix) isothiazolyl
      (x) imidazolyl
      (xi) benzimidazolyl
      (xii) tetrazolyl
      (xiii) pyrazinyl
      (xiv) pyrimidyl
      (xv) quinolyl
      (xvi) isoquinolyl
      (xvii) benzofuryl
      (xviii) isobenzofuryl
      (xix) benzothienyl
      (xx) pyrazolyl
      (xxi) isoindolyl
      (xxii) purinyl
      (xxiii) carbazolyl
      (xxiv) isoxazolyl
      (xxv) thiazolyl
      (xxvi) oxazolyl
      (xxvii) benzthiazolyl
      (xxviii) benzoxazolyl,
      and the like
   d) Substituted aryl wherein the aryl and substituents are selected from 5b It will be understood that there is a wide variety of polymer/Formula 1 combinations that are useful in forming the solid phase templates in accordance with the present invention. Accordingly, the organic chemist will choose the solid phase template to be compatible with the solvents and reaction conditions that are used to create the final molecule of interest.

The final step in the solid phase synthesis is the cleavage of the desired compounds from the polymeric support (i.e. Polymer-X-L-monomer, wherein the monomer is obtained by reacting compounds of Formula 1 with a plurality of chemical transformations) as described above to provide polymer-A (insoluble) and B-L-monomer. The cleavage can be carried out under acidic conditions such as by way of example and without limitation, using $CF_3CO_2H$ or under basic/nucleophilic conditions, for example utilizing dimethyl amine and hydroxylamine as the cleaving agent. Also, cleavage can be carried out under neutral conditions such as, for example and without limitation photolysis or pyrolysis.

Some preferred examples of the core compounds which contains the X-L-NH linkage are all of the natural and unnatural amino acids of the R- or S-configuration, for example alanine, arginine, aspartic acid, asparagine, cysteine, glutamic acid, glutamine, histidine, isoleucine, leucine, lysine, methionine, proline, phenylalanine, serine, threonine, tryptophan, tyrosine, ornithine, 2,3-diaminopropionic acid, 2,4-diaminobutyric acid. Additional examples include α,α-substituted amino acids like cycloleucine and the like; homo-amino acids like homophenylalanine and the like; synthetic amino acids like napthylalanines, pentafluorophenylalanine, biphenylalaninies and the like (Roberts, D. C.; Vellaccio, F. in "The Peptides, Volume 5" (Gross, E. and Meienhofer, J., Eds.) Academic Press, New York, 1983, pp342–449); N-substituted glycine derivatives; β-amino acids like β-alanine and the like; γ-amino acids like statine and the like; dipeptides and polypeptides.

Additional examples of preferred L groups of the core compounds are bi- or trisubstitued aromatic and polycyclic aromatic structures containing at least one amino or aminoalkyl function and at least one other nucleophilic functional group (—XH) as defined above.

EXAMPLES

The following examples are by way of illustration of various aspects of the present invention and are not intended to be limiting thereof.

General Procedures-Reagent Systems and Test Methods

Anhydrous solvents were purchased from Aldrich Chemical Company and used directly. Resins were purchased from Advanced ChemTech, Louisville, Ky., and used directly. The loading level ranged from 1.1 to 0.35 mmol/g. Unless otherwise noted, reagents were obtained from commercial suppliers and used without further purification. Preparative thin layer chromatography was preformed on silica gel precoated glass plates (Whatman PK5F, 150 Å, 1000 μm) and visualized with UV light, and/or ninhydrin, p-anisaldehyde, ammonium molybdate, or ferric chloride. NMR spectra were obtained on a Varian Mercury 300 MHz spectrometer. Chemical shifts are reported in ppm. Unless otherwise noted, spectra were obtained in $CDCl_3$ with residual $CHCl_3$ as an internal standard at 7.26 ppm. IR spectra were obtained on a Midac M1700 and absorbances are listed in inverse centimeters. HPLC/MS analysis were performed on a Hewlett Packard 1100 with a photodiode array detector coupled to a Micromass Platform II electrospray mass spectrometer. An evaporative light scattering detector (Sedex 55) was also incorporated for more accurate evaluation of sample purity. Reverse phase columns were purchased from YMC, Inc. (ODS-A, 3 μm, 120 Å, 4.0×50 mm).

Solvent system A consisted of 97.5% MeOH, 2.5% $H_2O$, and 0.05% TFA. Solvent system B consisted of 97.5% $H_2O$, 2.5% MeOH, and 0.05% TFA. Samples were typically acquired at a mobile phase flow rate of 2 ml/min involving a 2 minute gradient from solvent B to solvent A with 5 minute run times. Resins were washed with appropriate solvents (100 mg of resin/1 ml of solvent). Technical grade solvents were used for resin washing.

General Procedures-Deprotection of Amine Resins

Fmoc protected amine resins were washed with DMF and then treated with 25% piperidine in DMF (1 ml/100 mg resin) for 5 minutes then with 25% piperidine in DMF for 30 minutes. The resulting resin was filtered and washed with DMF (2×), MeOH/DCM (3×), and dry DCM (2×) to give free amine resin.

Boc protected amine resins were washed with DCM and then treated with 25% TFA in DCM (1 ml/100 mg resin) for 3 minutes then with 25% TFA in DCM for 30 minutes. The resulting resin was filtered and washed with DCM (2×), 1 M DIPEA in DCM (2×), MeOH/DCM (3×), and dry DCM (2×) to give free amine resin.

General Procedures-Cleavage of the Products from the Resins.

The final product was liberated from the Wang or Rink resin by exposure to 25% TFA in DCM for 30 min to 1 hour. The resin was filtered and the filtrate was collected in a flask containing toluene. The resin was washed with DCM (2×) and the combined filtrates were concentrated under vacuum. The resulting residue was dissolved in acetonitrile, then a same amount of water was added and the resulting solution was evaporated in vacuo to give the crude product.

The final product from the hydroxymethyl polystyrene resin was cleaved by treatment with a 1:1 mixture of 48% aqueous $MeNH_2/THF$ at room temperature for 24 h. In this case, N-methyl amide was obtained. The corresponding hydroxamic acid could be obtained from derivatized hydroxymethyl polystyrene by 1–2 h exposure to a 3:2:1 mixture of 2 M $NH_2OH$ in $MeOH/THF/Et_3N$ at room temperature.

Example I

The preparation of the amino-ketone template having the formula 1e was as follows. An amine containing resin (500 mg, 0.35 mmol) (Formula 1) was freshly prepared from the corresponding Fmoc resin as described above, then washed with dry THF (3×) under a nitrogen atmosphere. The resin was slurried in 1.6 mL of dry THF and a 1.0 M solution of N,N-diisopropylethylamine in THF (1.6 mL, 1.6 mmol) was added in one portion. A 0.5 M solution of an appropriate α-bromoketone in dry dichloroethane (2.1 mL, 1.05 mmol) was added and the resulting slurry was stirred or shaken at room temperature for 3 to 12 hours. For the Wang- and Rink-type resins exact reaction time was judged by removal of an aliquot which was filtrated, washed with DCM (2×), MeOH/DCM (3×), DCM (2×) and treated with 20–50% TFA in DCM for 10 minutes. Immediate evaporation follow ed by HPLC an lysis of the resulting residue allowed accurate determination of correct reaction time for each type of resin. After appropriate reaction time, the reaction mixture was filtrated, then washed with DCM (2×), and MeOH/DCM (3×). The resin was further washed with dry DCM (2×) and kept under a nitrogen atmosphere after drying.

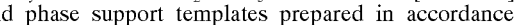
Polymer-X-L-NH—$CHR_2$—$COR_3$         [Formula 1e]

Solid phase support templates prepared in accordance with Example I were reacted with plurality of chemical transformations followed by cleavage of the desired compounds using well understood techniques and appropriate cleavage reagents to provide the desired molecules or monomers. Some of these transformations are shown below

Example II
Imidazole Preparation

The polymer-bound amino-ketone of Example I (0.1 /mmol) was suspended in a 1.0 M solution of carboxylic acid in DMF (1 mL,/mmol). A 1.0 M solution of DIC in DMF (1 mL,/mmol) was added. The resulting mixture was shaken at room temperature for 12 h. The resin was then filtered, and washed with DMF (2×), MeOH/DCM (3×), and DCM (2×). To the dried resin were added 500 mg of $NH_4OAc$ and 1.2 mL of HOAc. The suspension was then to room temperature, the resin was filtered, washed with HOAc (2×), DMF (2×), DCM (2×), 1.0 M DIEA in DCM (2×), MeOH/DCM (3×), and DCM (2×). The resulting resin was then subjected under General Procedures-Cleavage of The polymer bound amino ketone 2a undergoes imidazole formation under standard conditions to provide the corresponding polymer bound imidazoles of general Formula 2b. Cleavage of the desired imidazoles of Formula 2b using the appropriate cleavage conditions afforded the imidazoles of general Formula 2c (Scheme 3)

Scheme 3

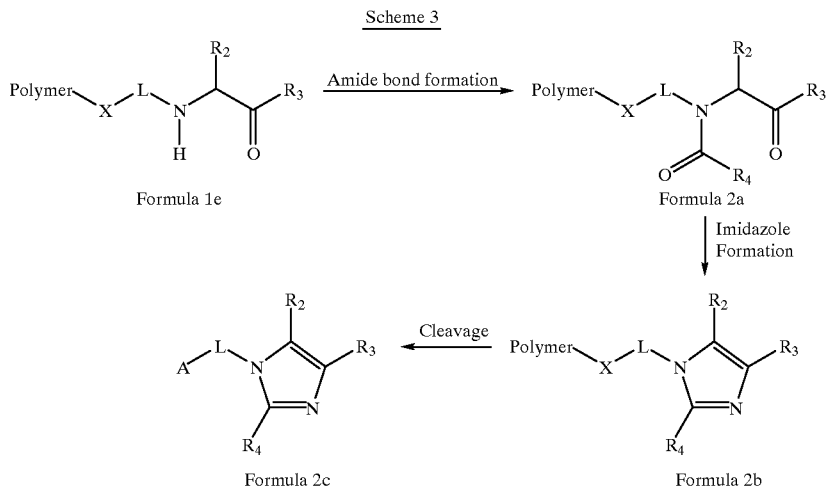

Example III

Preparation of Benzodiazepine Derivatives

The solid support reaction compound of Example/ (Formula 1e) is reacted with a series of β-aminocarboxylic acids to provide the α-aminoamides (Formula 3a) linked on the polymer. A polymer-bound amino-ketone (0.1 mmol) was slurried in a 0.5 M solution of anthranilic acid in THF (1.6 mL, 0.8 mmol) and a 1.0 M solution of DIEA in DCE (1.6 mmol). A 0.5 M solution of PyBrOP in DCE (1.6 mL, 0.8 mmol) was then added, and the suspension was shaken at room temperature for 18 h. The polymer was filtered and washed with DMF (2×), MeOH/DCM (3×), and DCM (2×). The dried resin was then treated with 1.5 mL of HOAc for 24 h, filtered and washed with DCM (2×), DMF (2×), MeOH/DCM (3×), and DCM (2×). The product was released from the resin by 25% TFA in DCM for 30 min at room temperature, followed by filtration, dilution, and concentration.

Formula 3a undergoes cyclization reaction under standard conditions to provide the diazepines of general Formula 3b, which upon cleavage using the appropriate cleaving reagent, the desired compounds of general Formula 3c are obtained (Scheme 4)

Scheme 4

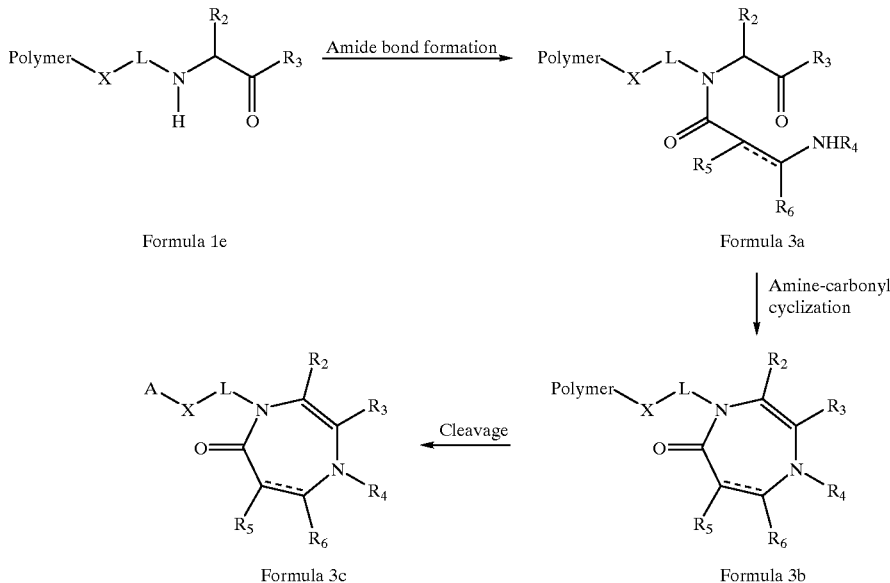

Example IV

Preparation of Imidazo[1,2-d][1,4]-diazepinone derivatives: L=CHR1CHR2, X=COO The imidazole was formed under the standard conditions as described above in which the carboxylic acid was an appropriate Boc protected α-amino acid. Then, the polymer-bound imidazole was treated with 20% TFA in DCM for 30 min at room temperature, filtered and washed with DCM (2×), 1.0 M DIEA in DCM (2×), MeOH/DCM (3×), and dry DCM (2×) to give free amine resin. The final product, imidazole-diazepinone, was released by the treatment with 5% Et3N in toluene at 100° C. for 12 h, followed by filtration, washing with THF (1×), and concentration. The residue was purified by silica gel chromatography

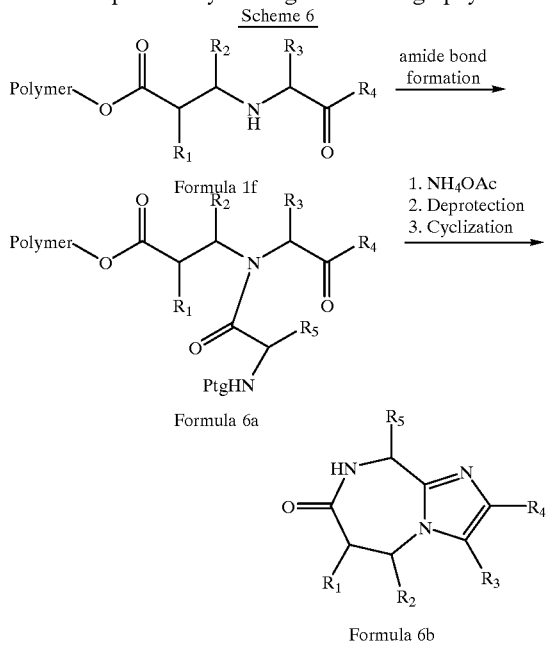

Scheme 6

Example V

Preparation of Pyrazine Derivatives:

The solid phase reaction component of Example I is reacted with a series of electrophiles such as sulfonyl chlorides ($R_4SO_2Cl$), isocyanates ($R_4N=C=O$), chloroformates ($R_4OCOCl$) to provide compounds of general formula 4a where Y=SO2, —CONH, —COO respectively. Treatment of compounds of general Formula 4a with a series of amines ($R_5NH_2$) provided the desired pyrazines of general formula 4b Fmoc protected amino acid solutions were prepared at 0.78 M in dry N-(methyl-2-pyrrolidinone containing 0.1% HOBT. 1-[3-(dimethylamino)propyl]-3-ethylcarbodiimide hydrochloride (EDC) was dispensed as a slurry in DMF (75 mg EDC suspended in 175 µL DMF).

To a polymer-bound α-amino-ketone (Formula 1e) (0.035 mmol) was added a suspension of EDC (75 mg, 0.42 mmol), in 175 µL of DMF. The pertinent Fmoc amino acid solution (450 µL, 0.35 mmol) was then added and the resulting slurry was stirred or shaken for 12 to 18 hours. The resin was filtered and washed with DMF (2×) then treated with 500 µL of 25% piperidine in DMF for 5 minutes then with 500 µL of 25% piperidine in DMF for 30 minutes. The resulting resin was filtered and washed with DMF (2×), MeOH/DCM (3×), and DCM (2×). The pyrazin-2-one derivatives were cleaved from Wang or Rink resin by exposure to 25% TFA in DCM for 30 min to 1 hour. The resin was filtered and the filtrate was collected in a flask containing 250 µL of toluene. The resin was washed and concentrated in vacuo. The resulting residue was dissolved in 250 µL of acetonitrile, then water (250 µL) was added and the solution was evaporated in vacuo to provide the crude product which was purified by silica gel chromatography.

When compounds of general Formula 4a are reacted with protected aminoacids derivatives using standard amide bond forming reactions followed by deprotecting the amine moiety, the desired pyrazines of general formula 4c are obtained. Cleavage from the polymer using suitable cleavage conditions provided compounds of general Formula 4d (Scheme 5)

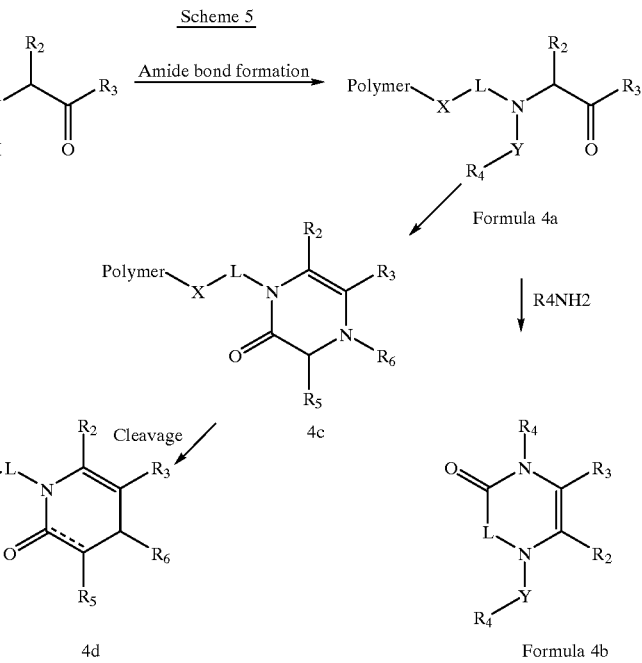

Scheme 5

Example VI

Preparation of Steroid mimics: L=CHR1 X=COO

The preparation of steroid mimics was carried out according to scheme 7 in the following manner. Fmoc protected amino acid solutions were prepared at 0.78 M in dry N-methyl-2-pyrrolidinone containing 0.1% HOBT. 1-[3-(dimethylamino)propyl]-3-ethylcarbodiimide hydrochloride (EDC) was dispensed as a slurry in DMF (75 mg EDC suspended in 175 μL DMF).

To a polymer-bound α-amino-ketone (0.035 mmol) was added a suspension of EDC (75 mg, 0.42 mmol), in 175 μL of DMF. The pertinent Fmoc amino acid solution (450 μL, 0.35 mmol) was then added and the resulting slurry was stirred or shaken for 12 to 18 hours. The resin was filtered and washed with DMF (2x) then treated with 500 μL of 25% piperidine in DMF for 5 minutes then with 500 μL of 25% piperidine in DMF for 30 minutes. The resulting resin was filtered and washed with DMF (2x), MeOH/DCM (3x), and DCM (2x). The pyrazin-2-one derivatives were cleaved from Wang resin by exposure to 25% TFA in DCM for 30 min to 1 hour. The resin was filtered and the filtrate was collected in a flask containing 250 μL of toluene. The resin was washed and concentrated in vacuo. The resulting residue was dissolved in 250 μL of acetonitrile, then water (250 μL) was added and the solution was evaporated in vacuo to provide the crude product which was purified by silica gel chromatography.

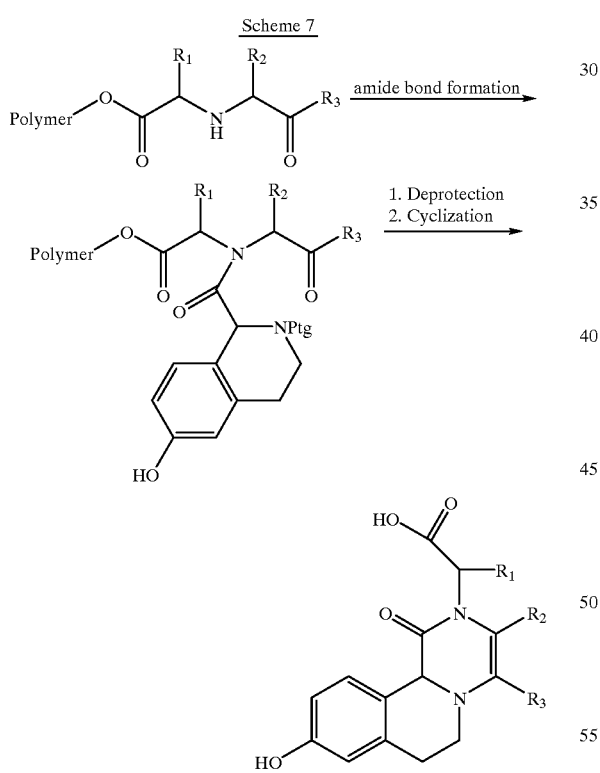

The following examples illustrate the synthesis of compounds useful as screening compounds in the search for compounds having pharmaceutical or therapeutic efficacy. These compounds were analysed in accordance with the General Procedures-Reagent Systems and Test Methods set forth above.

Example VII–VIII

A solid phase reaction template having the following formula was prepared according to Example I.

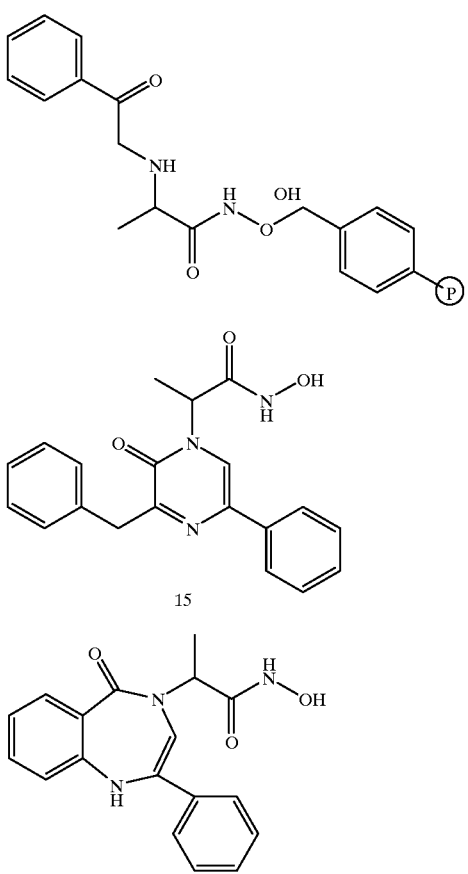

Utilizing the solid phase template the following compounds, identified as compound 15 and compound 25 were prepared in the manner described above in the General Procedures.

Analysis of the Compounds Developed the Following Data:

Compound 15: 2-(3-Benzyl-2-oxo-5-phenyl-2H-pyrazin-1-yl)-N-hydroxy-propionamide. $^1$H NMR (CDCl$_3$+CD$_3$OD) δ 7.90 (s, 1 H), 7.75 (d, J=8.4 Hz, 2 H), 7.20–7.40 (m, 8 H), 5.41 (q, 1 H), 4.18 (s, 2 H), 1.62 (d, 3 H). MS (ES) m/e (relative intensity): 350 (M+H$^+$, 50).

Compound 25: N-Hydroxy-2-(5-oxo-2-phenyl-1,5-dihydrobenzo[e][1,4]diazepin-4-yl)-propionamide. MS (ES) m/e 324 (M+H$^+$).

Example IX

A solid phase reaction template having the following formula was prepared according to Example I.

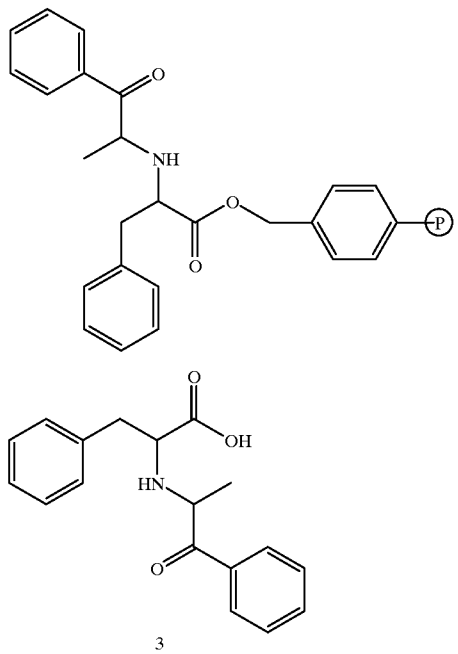

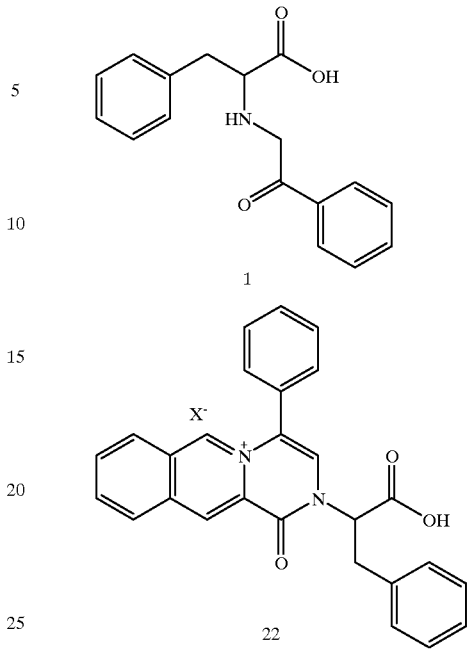

Utilizing the solid phase template the following compounds, identified as compound 3 was prepared in the manner described above in the General Procedures.

Analysis of the Compound 3 Developed the Following Data:

Compound 3: 2-[2-phenyl-1-methyl-2-oxo-ethylamino]-3-phenyl-propionic acid. MS (ES) m/e (relative intensity): 298 (M+H$^+$, 75).

Example X

A solid phase reaction template having the following formula was prepared according to Example I.

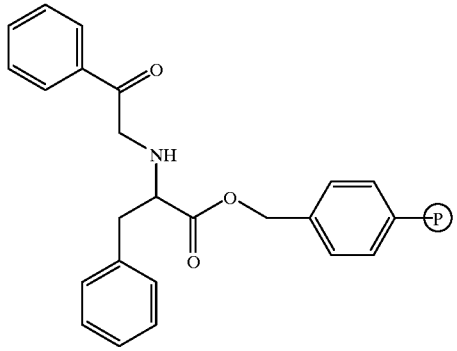

Utilizing the solid phase template the following compounds, identified as compounds 1 and 22 were prepared in the manner described above in the General Procedures.

Analysis of the Compounds 1 and 22 Developed the Following Data:

Compound 1: 2-(2-Oxo-2-phenyl-ethylamino)-3-phenyl-propionic acid. $^1$H NMR (DMSO-D$_6$) δ 8.05 (d, J=8.4 Hz, 2 H), 7.79 (t, J=7.5 Hz, 1 H), 7.66 (t, J=7.5 Hz, 2 H), 7.40 (br s, 5 H), 4.65 (d, J=18.6 Hz, 1 H), 4.54 (d, J=18.6 Hz, 1 H), 3.95 (t, J=6.9 Hz, 1 H), 3.21 (m, 2 H). MS (ES) m/e (relative intensity): 284 (M+H$^+$, 100), 238 (90).

Compound 22: 2-(1-Carboxy-2-phenyl-ethyl)-1-oxo-4-phenyl-1,2-dihydro-pyrazino[1,2-b]isoquinolin-5-ylium; trifluoro-acetate. $^1$H NMR (CD$_3$OD) δ 9.63 (s, 1 H), 9.52 (s, 1 H), 8.56 (d, J=7.5 Hz, 1 H), 8.40 (t, J=7.5 Hz, 1 H), 8.30 (t, J=7.5 Hz, 1 H), 7.80 (m, 2 H), 7.60 (m, 2 H), 7.43 (m, 5 H), 5.95 (m, 1 H), 4.40 (s, 1 H), 3.70 (m, 1 H). MS (ES) m/e (relative intensity): 421 (M$^+$, 38), 377 (100).

Example XI

A solid phase reaction template having the following formula was

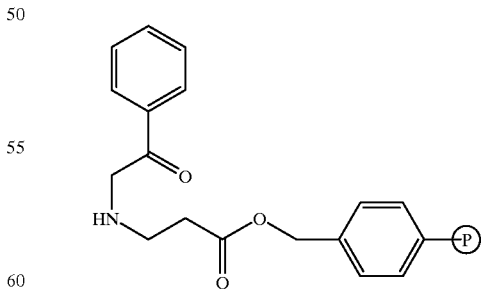

prepared according to Example I

Utilizing the solid phase template the following compounds, identified as compounds 5, 6, 7, 8, 9, 10, 11, 12, 13, 14 and 26 were prepared in the manner described above in the General Procedures.

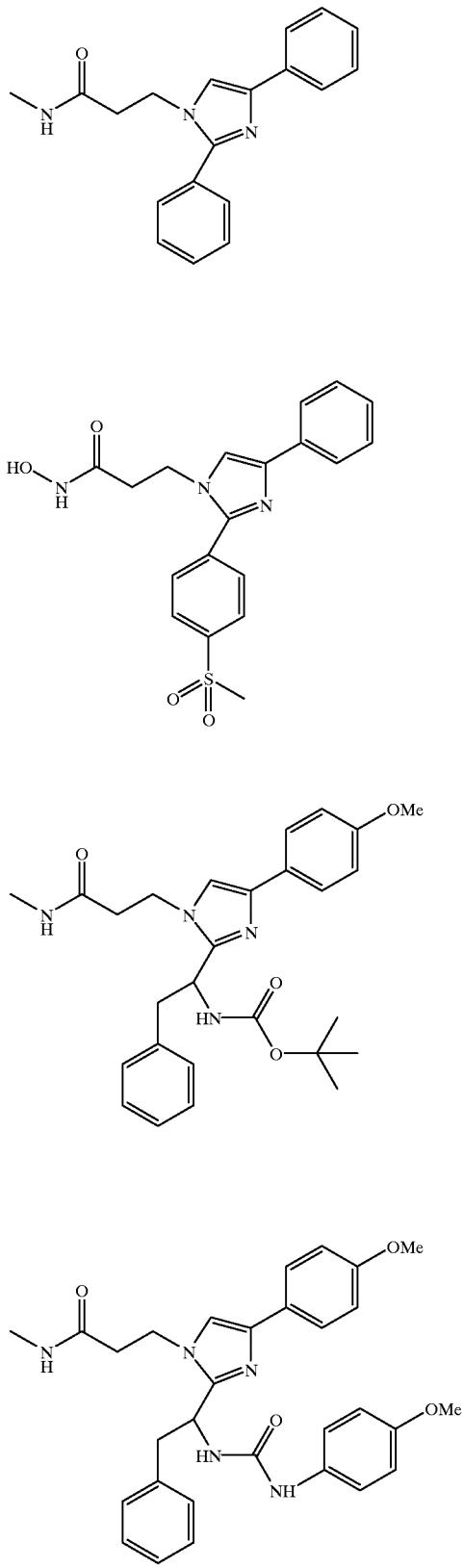
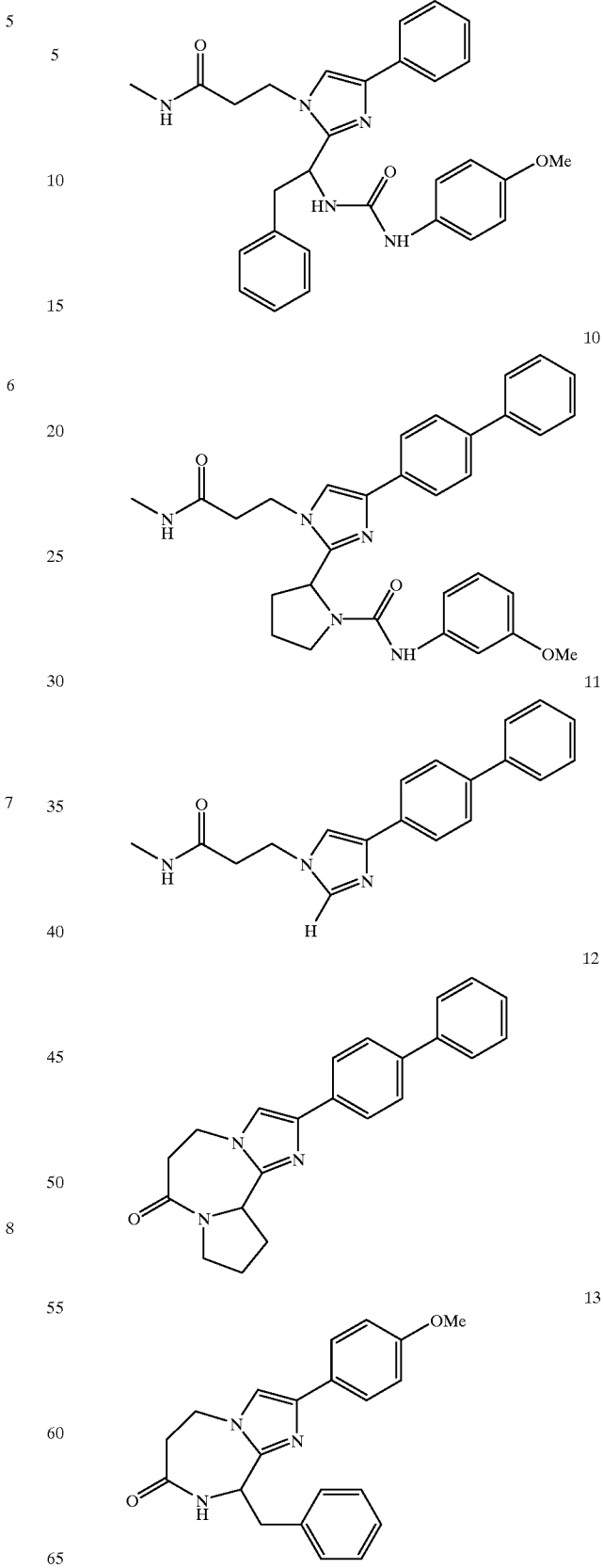

-continued

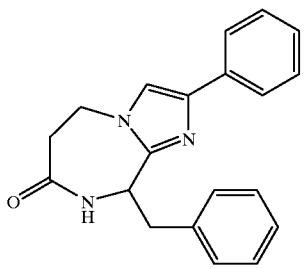

14

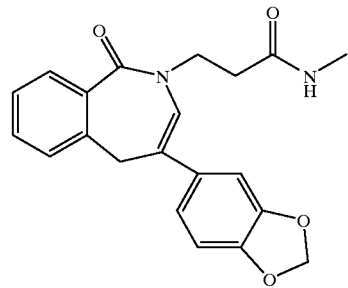

26

Analysis of the Compounds Developed the Following Data:

Compound 5: 3-(2,4-Diphenyl-imidazol-1-yl)-N-methyl-propionamide. MS (ES) m/e (relative intensity): 306 (M+H+, 100).

Compound 6: N-Hydroxy-3-[2-(4-methanesulfonyl-phenyl)-4-phenyl-imidazol-1-yl]-propionamide. $^1$H NMR (CD$_3$OD) δ 8.26 (d, J=8.4Hz, 2 H), 8.09 (d, J=8.4 Hz, 2 H), 7.93 (s, 1 H), 7.85 (m, 2 H), 7.44–7.55 (m, 3 H), 4.54 (t, J=6.6 Hz, 2 H), 3.29 (s, 3 H), 2.73 (t, J=6.6 Hz, 2 H). MS (ES) m/e (relative intensity): 386 (M+H+, 100).

Compound 7: {1-[4-(4-Methoxy-phenyl)-1-(2-methylcarbamoyl-ethyl)-1H-imidazol-2-yl]-2-phenyl-ethyl}-carbamic acid tert-butyl ester. $^1$H NMR (CDCl$_3$) δ 7.78 (d, J=8.4 Hz, 2 H), 7.33–7.38 (m, 3 H), 7.21–7.24 (m, 2 H), 7.05 (d, J=8.4 Hz, 2 H), 6.97 (s, 1 H), 5.90 (br s, 1 H), 5.60 (br s, 1 H), 5.50 (m, 1 H), 3.96 (s, 3 H), 4.10 (m, 1 H), 3.81 (m, 1 H), 3.48 (dd, J=10.2 Hz, 12 Hz, 1 H), 3.38 (dd, J=12 Hz, 5.4 Hz, 1 H), 2.68 (d, J=4.8 Hz, 3 H), 2.00 (m, 2 H), 1.53 (s, 9 H). MS (ES) m/e (relative intensity): 479 (M+H+, 92), 423 (100).

Compound 8: 3-(4-(4-Methoxy-phenyl)-2-{1-[3-(4-methoxy-phenyl)-ureido]-2-phenyl-ethyl}-imidazol-1-yl)-N-methyl-propionamide. $^1$H NMR (CDCl$_3$) δ 7.90 (br s, 1 H), 7.70 (d, J=8.4 Hz, 2 H), 7.36 (m, 3 H), 7.21 (m, 2 H), 7.01 (m, 4 H), 6.80 (d, J=9.0 Hz, 2 H), 6.68 (d, J=9.0 Hz, 2 H), 6.69 (s, 1 H), 5.25 (m, 1 H), 4.05 (m, 1 H), 3.92 (s, 3 H), 3.80 (s, 3 H), 3.55 (m, 3 H), 3.05 (m, 1 H), 2.25 (m, 1 H), 2.54 (d, J=4.8 Hz, 3 H). MS (ES) m/e (relative intensity): (528 (M+H+, 100).

Compound 9: 3-(2-{1-[3-(4-Methoxy-phenyl)-ureido]-2-phenyl-ethyl}-4-phenyl-imidazol-1-yl)-N-methyl-propionamide. $^1$H NMR (CDCl$_3$) δ 7.95 (br s, 1 H), 7.80 (d, J=7.2 Hz, 2 H), 7.47 (t, J=7.8 Hz, 2 H), 7.36 (m, 5 H), 7.21 m, 2 H), 7.13 (s, 1 H), 6.78 (d, J=8.7 Hz, 2 H), 6.67 (d, J=8.7 Hz, 2 H), 6.68 (s, 1 H), 5.27 (m, 1 H), 4.15 (m, 1 H), 3.79 (s, 3 H), 3.56 (m, 3 H), 3.05 (m, 1 H), 2.53 (d, J=4.8 Hz, 3 H), 2.25 (m, 1 H). MS (ES) m/e (relative intensity): 498 (M+H+, 100).

Compound 10: 2-[4-Biphenyl-4-yl-1-(2-methylcarbamoyl-ethyl)-1H-imidazol-2-yl]-pyrrolidine-1-carboxylic acid (3-methoxy-phenyl)-amide. $^1$H NMR (CDCl$_3$) δ 7.90 (d, J=8.4 Hz, 2 H), 7.71 (m, 4 H), 7.55 (t, J=7.2 Hz, 2 H), 7.45 (d, J=7.0 Hz, 1 H), 7.25 (m, 2 H), 7.09 (s, 1 H), 6.95 (d, J=8.4 Hz, 1 H), 6.82 (br s, 1 H), 6.67 (m, 2 H), 5.32 (m, 1 H), 4.49 (m, 3 H), 3.94 (m, 1 H), 3.81 (s, 3 H), 2.67 (d, J=4.8 Hz, 3 H), 2.24–3.20 (m, 7 H). MS (ES) m/e (relative intensity): 524 (M+H+, 100).

Compound 11: 3-(4-Biphenyl-4-yl-imidazol-1-yl)-N-methyl-propionamide. $^1$H NMR (CDCl$_3$) δ 7.37–7.96 (m, 11 H), 5.55 (m, 1 H), 4.48 (t, J=6.3 Hz, 3 H), 2.93 (d, J=4.8 Hz, 2 H), 2.74 (t, J=6.3 Hz, 2 H). MS (ES) m/e (relative intensity): 306 (M+H+, 100).

Compound 12: 2-Biphenyl-4-yl-4,5,7,8,9,9a-hexahydro-1,3a,6a-triazacyclopenta[e]azulen-6-one. $^1$H NMR (CDCl$_3$) δ 7.92 (d, J=8.4 Hz, 2 H), 7.30 (m, 5 H), 7.56 (d, J=8.4 Hz, 2 H), 7.31 (s, 1 H), 5.16 (m, 1 H), 4.45 (m, 2 H), 3.86 (m, 2 H), 2.96 (m, 2 H), 2.64 (m, 2 H), 2.10 (m, 2 H). MS (ES) m/e (relative intensity): 344 (M+H+, 90).

Compound 13: 8-Benzyl-2-(4-methoxy-phenyl)-4,5,7,8-tetrahydro-1,3a,7-triaza-azulen-6-one. $^1$H NMR (CDCl$_3$) δ 7.90 (d, J=9.0 Hz, 2 H), 7.48 (m, 5 H), 7.19 (s, 1 H), 7.05 (d, J=9.0 Hz, 2 H), 5.94 (m, 1 H), 5.09 (m, 1 H), 4.38 (m, 2 H), 4.08 (dd, J=3.6 Hz, 14 Hz, 1 H), 3.96 (s, 3 H), 3.21–3.37 (m, 2 H), 2.85–2.89 (m, 1 H). MS (ES) (relative intensity): 348 (M+H+, 100).

Compound 14: 8-Benzyl-2-phenyl-4,5,7,8-tetrahydro-1,3a,7-triaza-azulen-6-one. MS (ES) m/e (relative intensity): 318 (M+H+, 100).

Compound 26: 3-(2-Benzo[1,3]dioxol-5-yl-5-oxo-1,5-dihydro-benzo[e][1,4]diazepin-4-yl)-N-methyl-propionamide. MS (ES) m/e 366 (M+H+).

Table 1 below sets forth the structure of additional compounds useful for screening for pharmaceutical and therapeutic efficacy which are synthesized by solid phase techniques using an amino-ketone solid phase reaction component of the present invention.

TABLE 1

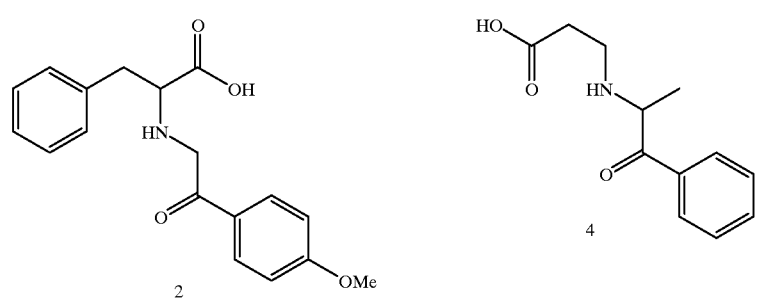

TABLE 1-continued
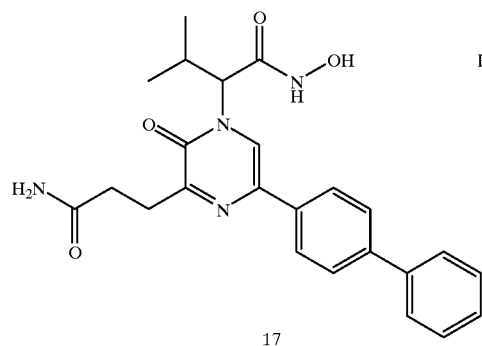
17
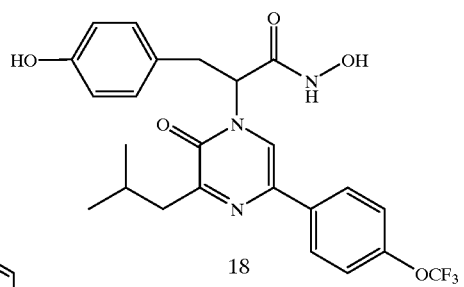
18
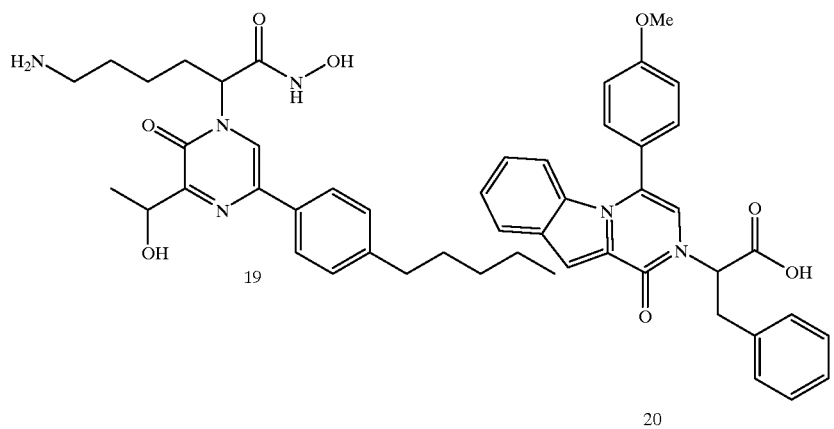
19
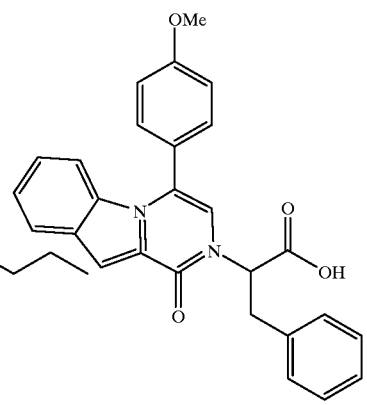
20
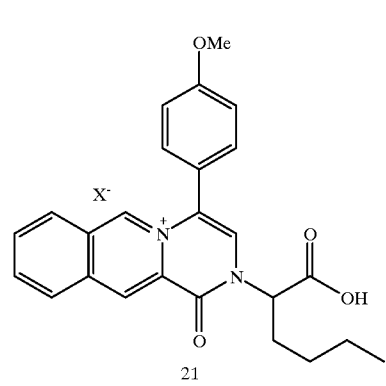
21
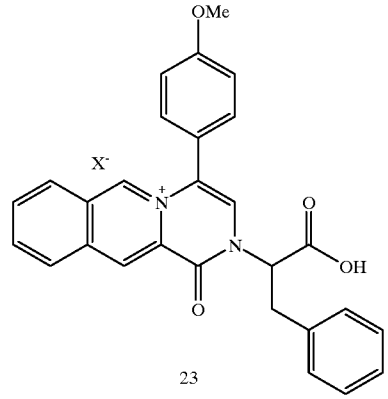
23

TABLE 1-continued

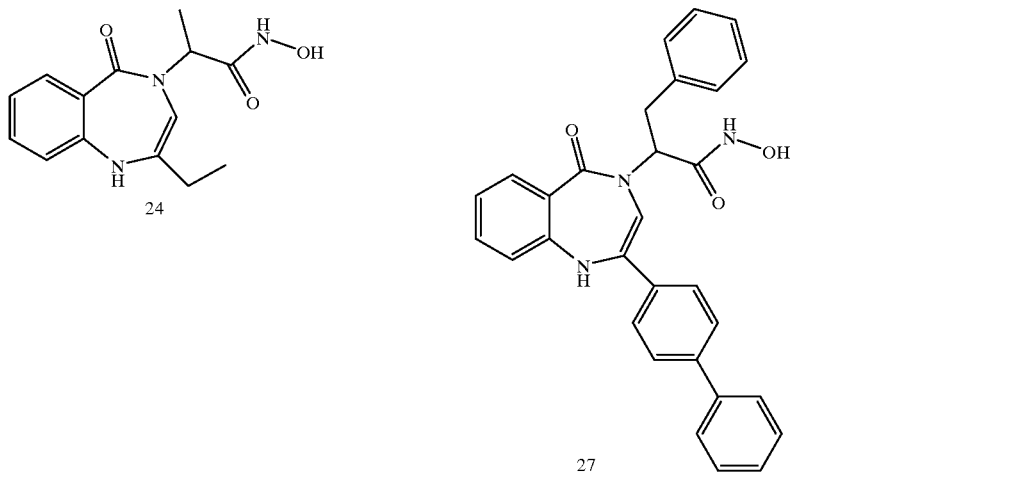

Analysis of the compounds set forth in Table 1 was conducted as described above in General Procedures-Reagent Systems and Test Methods above. The results are set forth below.

Compound 2: 2-[2-(4-Methoxy-phenyl)-2-oxo-ethylamino]-3-phenyl-propionic acid. $^1$H NMR (DMSO-D$_6$) δ 7.98 (d, J=8.4 Hz, 2 H), 7.36 (br s, 5 H), 7.13 (d, J=8.4 Hz, 2 H), 4.27 (d, J=17.7 Hz, 1 H), 4.12 (d, J=17.7 Hz, 1 H 3.94 (s, 3 H). MS (ES) m/e (relative intensity): 314 (M+H$^+$, 85), 268 (25).

Compound 4: 3-(1-Methyl-2-oxo-2-phenyl-ethylamino)-propionic acid. MS (ES) m/e (relative intensity): 222 (M+H$^+$, 90).

Compound 17: 2-[3-Isopropyl-5-(2-methoxy-phenyl)-2-oxo-2H-pyrazin-1-yl]-3-methyl-pentanoic acid. MS (ES) m/e (relative intensity): 473 (M+H$^+$, 100).

Compound 18: N-Hydroxy-3-(4-hydroxy-phenyl)-2-[3-isobutyl-2-oxo-5-(4-trifluoromethoxy-phenyl)-2H-pyrazin-1-yl]-propionamide. MS (ES) m/e (relative intensity): 492 (M+H$^+$, 100).

Compound 19: 6-Amino-2-[3-methyl-2-oxo-5-(4-trifluoromethoxy-phenyl)-2H-pyrazin-1-yl]-hexanoic acid hydroxyamide. MS (ES) m/e (relative intensity): 415 (M+H$^+$, 100).

Compound 20: 2-[4-(4-Methoxy-phenyl)-1-oxo-1 H-pyrazino[1,2-α]indol-2-yl]-3-phenyl-propionic acid. $^1$H NMR (CD$_3$OD) δ 7.92 (d, J=7.0 Hz, 1 H), 6.90–7.30 (m, 12 H), 6.55 (d, J=7.0 Hz, 1 H), 6.15 (s, 1 H), 5.65 (m, 1 H), 4.95 (m, 1 H), 4.00 (s, 3 H), 3.90 (m, 2 H), 3.65 (m, 1 H). MS (ES) m/e (relative intensity): 439 (M+H$^+$, 30).

Compound 21: 2-(1-Carboxy-pentyl)-4-(4-methoxy-phenyl)-1-oxo-1,2-dihydro-pyrazino[1,2-b]isoquinolin-5-ylium; trifluoro-acetate. $^1$H NMR (CD$_3$OD) δ 9.75 (d, J=10.0 Hz, 2 H), 8.62 (m, 2 H), 8.40 (t, J=7.0 Hz, 1 H), 8.30 (t, J=7.0 Hz, 1 H), 7.70 (d, J=8.0 Hz, 2 H), 7.35 (d, J=8.0 Hz, 2 H), 5.70 (m, 1 H), 4.50 (s, 1 H), 4.10 (s, 3 H), 2.45 (m, 1 H), 2.25 (m, 1 H), 2.00 (m, 1 H), 1.90 (m, 1 H), 1.50 (m, 2 H), 1.00 (m, 3 H). MS (ES) m/e (relative intensity): 417 (M$^+$, 60).

Compound 23: 2-(1–Carboxy-2-phenyl-ethyl)-4-(4-methoxy-phenyl)-1-oxo-1,2-dihydro-pyrazino[1,2-b] isoquinolin-5-ylium; trifluoro-acetate. $^1$H NMR (CDCl$_3$) δ 9.40 (d, J=6.6 Hz, 2 H), 8.31 (m, 2 H), 8.13 (t, J=6.0 Hz, 1 H), 7.98 (m, 1 H), 7.10 (m, 9 H), 6.84 (m, 1 H), 4.26 (s, 1 H), 3.90 (s, 3 H), 3.58 (m, 1 H). MS (ES) m/e (relative intensity): 451 (M$^+$, 100).

Compound 24: 2-(2-Ethyl-5-oxo-1,5-dihydro-benzo[e][1,4]diazepin-4-yl)-N-hydroxy-propionamide. MS (ES) m/e 276 (M+H$^+$).

Compound 26: 3-(2-Benzo[1,3]dioxol-5-yl-5-oxo-1,5-dihydro-benzo[e][1,4]diazepin-4-yl)-N-methyl-propionamide. MS (ES) m/e 366 (M+H$^+$).

Compound 27: 2-(2-Biphenyl-4-yl-5-oxo-1,5-dihydro-benzo[e][1,4]diazepin-4-yl)-N-hydroxy-3-phenyl-propionamide. MS (ES) m/e 476 (M+H$^+$).

Having described the invention I claim:

1. A solid phase reaction component for the production of an amino containing chemical compound in a reaction media, said solid phase reaction component comprising an amino-ketone core compound linked to a polymer substrate, said reaction component being insoluble in said reaction media.

2. The solid phase reaction component of claim 1 having the formula:

Polymer-X-L-NH(CR$_1$R$_2$)$_n$COR$_3$ wherein:
n=1 or 2; X is a moiety that forms a covalent bond to join said polymer and said amino-ketone core compound; L is a multifunctional monomer carrying a first functional group that forms a covalent bond with X and a second functional group comprising an amine and L, R$_1$, R$_2$ and R$_3$ are selected from the group consisting of alkyl, alkyl-aryl, alkenyl, alkenyl-aryl groups having up to 6 carbon atoms and substituted forms thereof.

3. The solid phase reaction component of claim 2 wherein said polymer is selected from the group of organic polymers consisting of polystyrene, polypropylene, polyethylene glycol, polyacrylamide, cellulose and combinations thereof.

4. The solid phase reaction component of claim 2 wherein said polymer is a composite of inorganic and organic substrates.

5. The solid phase reaction component of claim 4 wherein said polymer is a composite consisting of polyacrylamide supported within a matrix of kieselghuhr particles.

6. The solid phase reaction component of claim 2 wherein X is selected from the functional group consisting of oxygen, an ester, an amide, sulfur, silicon, and carbon.

7. The solid phase reaction component of claim 2 wherein substituents of the substituted forms of L, R$_1$, R$_2$ and R$_3$ are selected from the group consisting of H, chloro, fluoro, bromo, iodo, nitro, cyano, and amino radicals, alkyloxy, alkyloxy aryl, aminocarbonyl, aminocarbonylalkyl-aryl, thioalkyl, thioalkyl-aryl, alkylsulfoxide, alkylsulfone, alkylsulfonamide, alkylsulfonamide aryl, alkylsulfoxide aryl, alkylsulfone aryl, alkyl aminocarbonylamino alkyl, alkyl aminocarbonylamino alkyl aryl, C1–C6 alkyloxycarbonyl alkyl, alkyloxycarbonyl alkyl aryl, carboxyalkyl, carboxyalkyl aryl carbonylalkyl, carbonylalkyl aryl, alkyloxycarbonylamino alkyl, alkyloxycarbonylamino alkyl aryl, Guanidino, alkylCOOH, alkylCONH2, alkenylCOOH, alkenyl CONH2 groups and said alkyl and aryl groups contain up to 6 carbon atoms.

8. The solid phase reaction component of claim 7 wherein said aryl group is mono, di- and tri-substituted and said aryl group is selected from the group consisting of phenyl, biphenyl, 2-naphthyl, 1-naphthyl, pyridyl, furyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, isoindolyl, purinyl, carbazolyl, isoxazolyl, thiazolyl, oxazolyl, benthiazolyl, and benzoxazolyl.

9. The solid phase reaction component of claim 7 suitable for the synthesis by solid phase reaction of imidazoles, indoles, thiazoles, diazepines, pyrazines, sulfonamides, ureas, pyridines, piperindines, steroids, mimimcs and the like having the formula:

Polymer-X-L-NH(CR$_1$R$_2$)$_n$COR$_3$.

10. The solid phase reaction component of claim 7 suitable for the synthesis by solid phase reaction of imidazoles, indoles, thiazoles, diazepines, pyrazines, sulfonamides, ureas, pyridines, piperindines, steroids, mimimcs and the like having the formula:

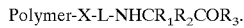

Polymer-X-L-NHCR$_1$R$_2$COR$_3$.

11. The solid phase reaction component of claim 7 suitable for the synthesis by solid phase reaction of highly functionalized imidazoles having the formula:

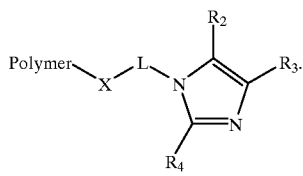

12. The solid phase reaction component of claim 7 suitable for the synthesis by solid phase reaction of highly functionalized diazepines having the formula:

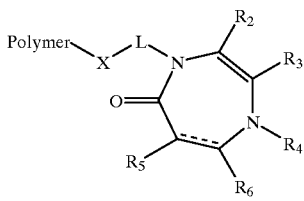

where R5 and R6 may be joined as a ring system or may be separate.

13. The solid phase reaction component of claim 2 wherein said polymer is selected from the group of inorganic polymers consisting of kieselghur, silica gel, and controlled pore glass and polymeric organic substrates consisting of polystyrene, polypropylene, polyethylene glycol, polyacrylamide and cellulose.

14. A method for the solid phase production of an amino containing compound in a reaction media comprising the steps of:

a. forming a solid phase support template comprising an amino-ketone core compound linked to a polymer substrate, said reaction template being insoluble in said reaction media and having the formula

Polymer-X-L-NH(CR$_1$R$_2$)$_n$COR$_3$ wherein: n=1 or 2; X is a moiety that forms a covalent bond to join said polymer and said amino-ketone core compound; L is a multifunctional monomer carrying a first functional group that forms a covalent bond with X and a second functional group comprising an amino group and L, R$_1$, R$_2$ and R$_3$ are selected from the group consisting of alkyl, alkyl-aryl, alkenyl, alkenyl-aryl groups having up to 6 carbon atoms and substituted forms thereof;

b. reacting said solid phase support template in said reaction media to form a reaction product comprising said desired amino containing compound linked to said resin;

c. cleaving said reaction product; and d. separating said desired amino containing compound from said reaction media.

15. The method of claim 14 wherein said desired amino containing compound is an imidazole that proceeds in accordance with the following solid phase reaction:

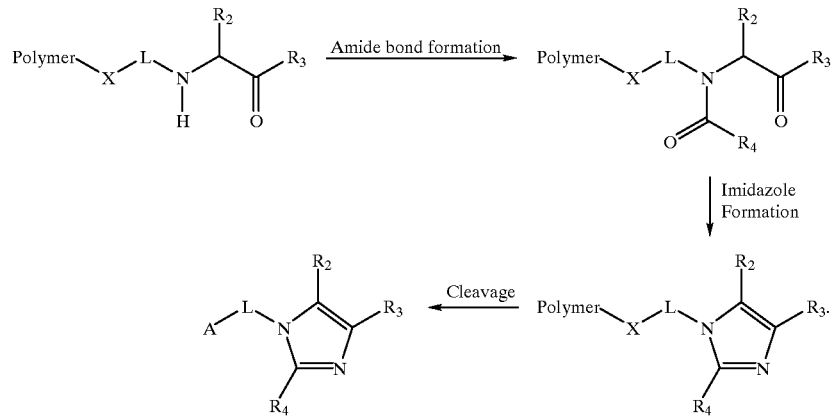

16. The method of claim 14 wherein said desired amino containing compound is a benzodiazepine derivative that proceeds in accordance with the following solid phase reaction:

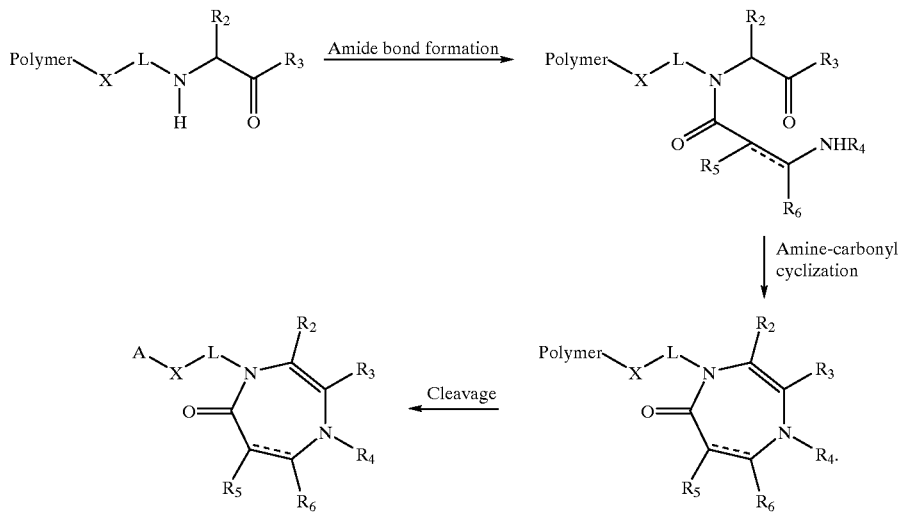

17. The method of claim 14 wherein said desired amino containing compound is an imidazole-diazepinone derivative that proceeds in accordance with the following solid phase reaction:

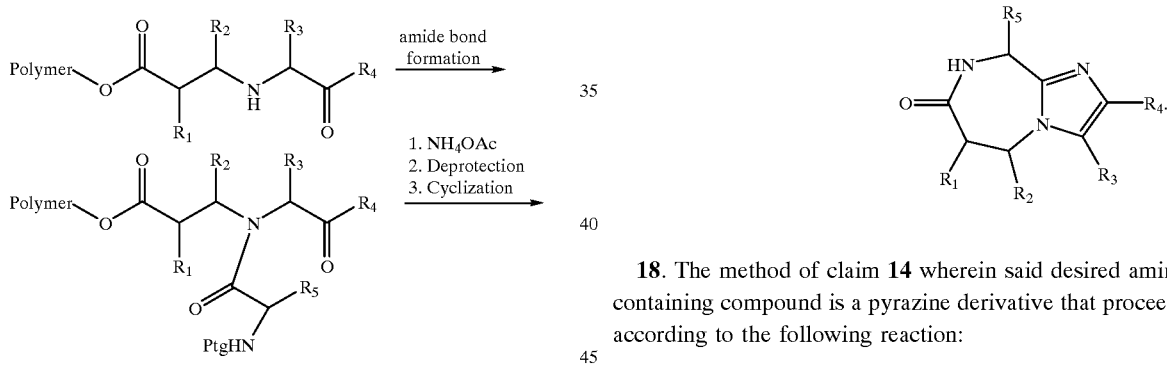

-continued

18. The method of claim 14 wherein said desired amino containing compound is a pyrazine derivative that proceeds according to the following reaction:

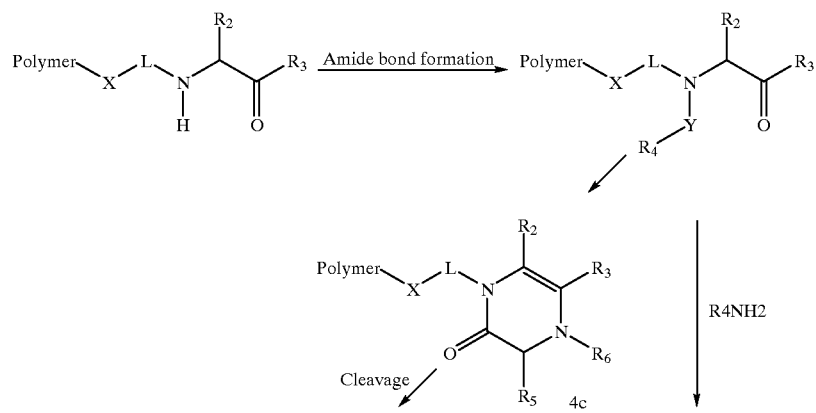

-continued

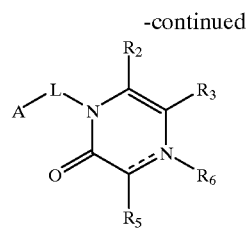 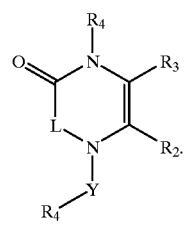

19. The method of claim 14 wherein said desired amino containing compound is a steroid mimic that proceeds according to the following reaction:

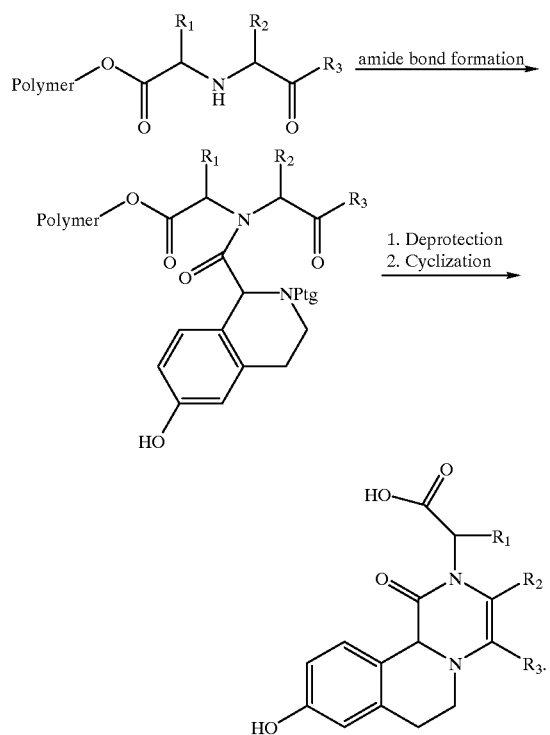

20. The method of claim 14 wherein said desired amino containing compound is 2-(3-benzyl-2-oxo-5-phenyl-2H-pyrazin-1-yl)-N-hydroxy-propionamide and said solid phase support has the formula:

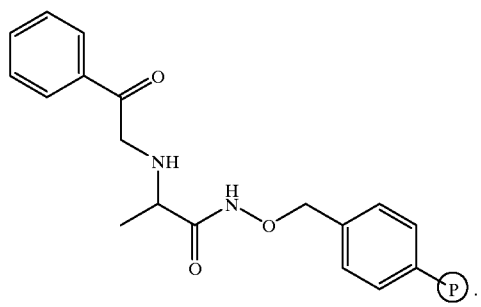

21. The method of claim 14 wherein said desired amino containing compound is N-hydroxy-2-(5-oxo-2-phenyl-1,5-dihydrobenzo[e][1,4]diazepin-4-yl)-propionamide and said solid phase has the formula:

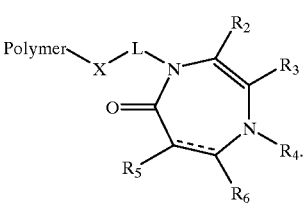

22. The method of claim 14 wherein said desired amino containing compound is 3-(1-methyl-2-oxo-2-phenyl-ethylamino)-propionic acid and said solid phase support has the formula:

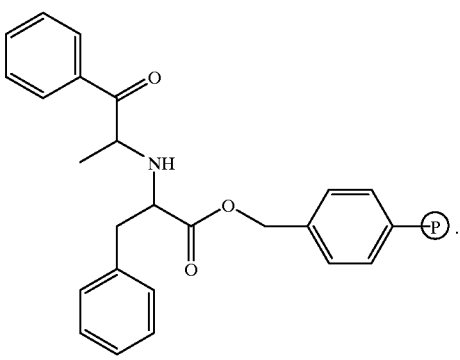

23. The method of claim 14 wherein said desired amino containing compound is 2-(1-carboxy-2-phenyl-ethyl)-1-oxo-phenyl-1,2-dihydro-pyrizinol[1,2-b]isoquinolin-5-ylium trifluoro-acetate and said solid phase support has the formula:

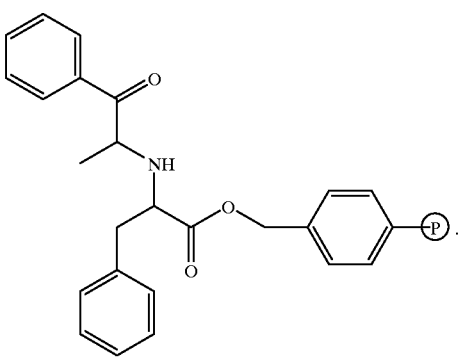

24. The method of claim 14 wherein said desired amino containing compound is 3-(2,4-diphenyl-imidazole-1-yl)-N-methyl-propionamide and said solid phase support has the formula:

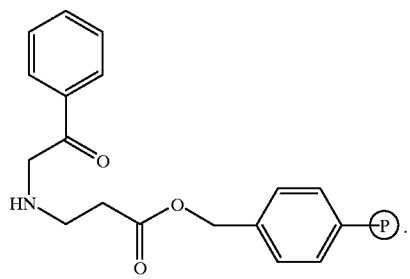

25. The method of claim 14 wherein said desired amino containing compound is N-hydroxy-3-[2-(4-methanesulfonyl-phenyl)-4-phenyl-imidazol-1-yl]-propionamide.
26. The method of claim 14 wherein said desired amino containing compound is 3-(2-{1-[3-(4-methoxy-phenyl)-uriedo]-2phenyl-ethyl}-4-phenyl-imidazol-1-yl)-N-methyl-propionamide.
27. The method of claim 14 wherein said desired amino containing compound is 8-benzyl-2-phenyl-4,5,7,8-tetrahydr-1,3a,7-triaza-azulen-6-one.
28. The method of claim 14 wherein said desired amino containing compound is 3-(2-benzo[1,3]dioxol-5-yl-5-oxo-1,5-dihydro-benzo[e][1,4]diazepin-4-yl)-N-methyl-propioamide.
29. The method of claim 14 wherein said desired amino containing compound is selected from the group having the formulae:

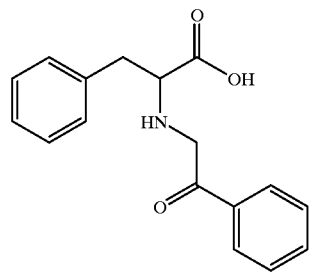

1

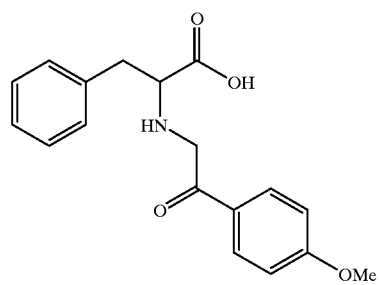

2

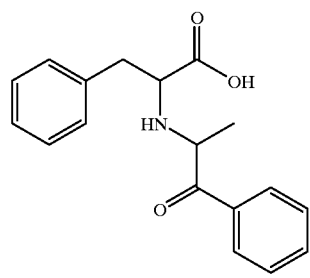

3

-continued

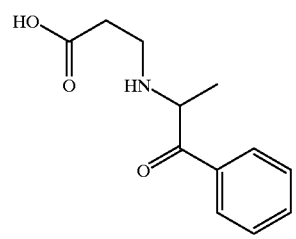

4

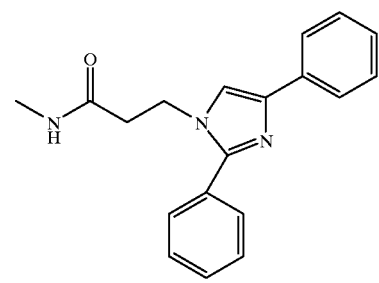

5

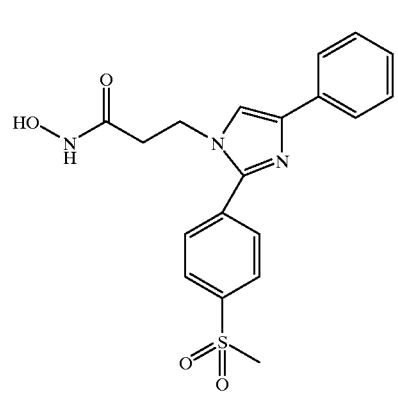

6

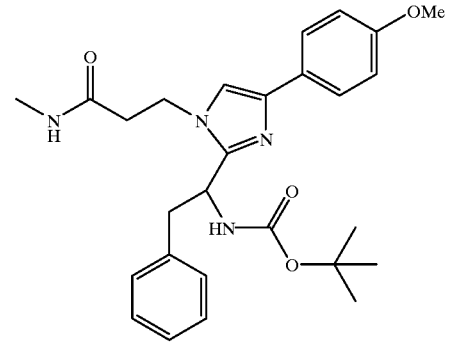

7

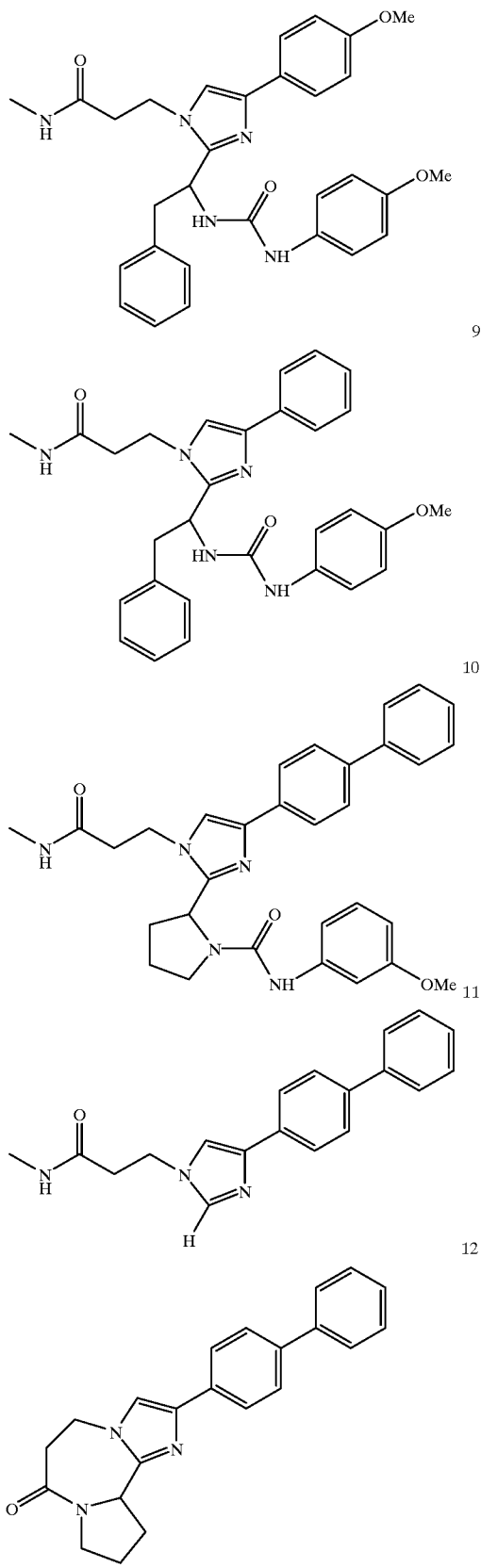

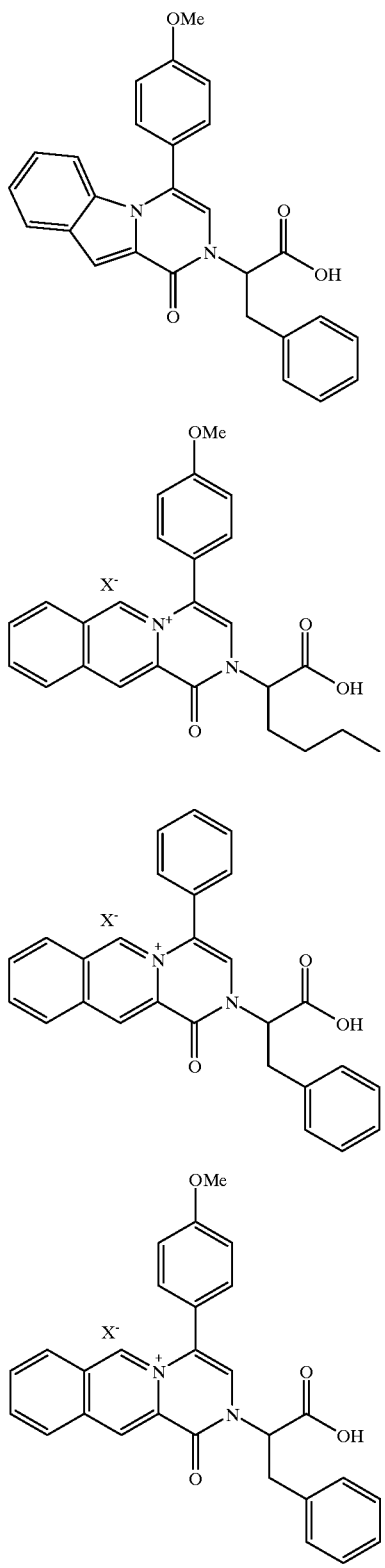
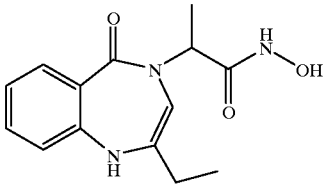
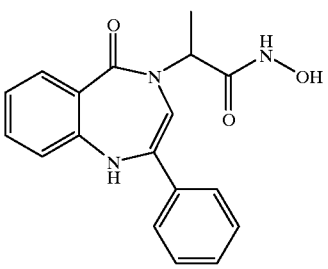
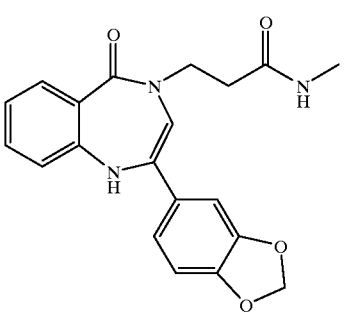
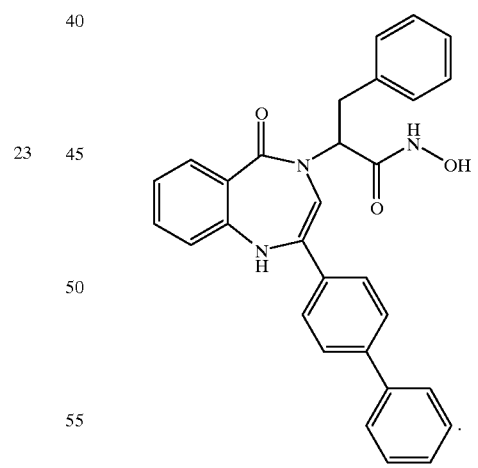
* * * * *